(12) United States Patent
Armbruster et al.

(10) Patent No.: US 10,226,293 B2
(45) Date of Patent: Mar. 12, 2019

(54) DRUG ELUTING SURGICAL SCREW

(71) Applicant: DePuy Synthes Products, Inc., Raynham, MA (US)

(72) Inventors: David A. Armbruster, West Chester, PA (US); Anurag Pandey, Fort Washington, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/808,932

(22) Filed: Nov. 10, 2017

(65) Prior Publication Data

US 2018/0070998 A1 Mar. 15, 2018

Related U.S. Application Data

(63) Continuation of application No. 15/174,054, filed on Jun. 6, 2016, now Pat. No. 9,833,271, which is a continuation of application No. 13/800,342, filed on Mar. 13, 2013, now Pat. No. 9,364,273.

(60) Provisional application No. 61/683,262, filed on Aug. 15, 2012.

(51) Int. Cl.
*A61B 17/86* (2006.01)
*A61B 17/00* (2006.01)

(52) U.S. Cl.
CPC ............ *A61B 17/864* (2013.01); *A61B 17/86* (2013.01); *A61B 17/8605* (2013.01); *A61B 17/866* (2013.01); *A61B 17/8615* (2013.01); *A61B 17/8685* (2013.01); *A61B 2017/00004* (2013.01); *A61B 2017/00889* (2013.01); *A61B 2017/00893* (2013.01)

(58) Field of Classification Search
CPC ..................................................... A61B 17/866
USPC ........................................... 424/422; 606/76
See application file for complete search history.

(56) References Cited

U.S. PATENT DOCUMENTS

| | | |
|---|---|---|
| 4,347,234 A | 8/1982 | Wahlig et al. |
| 4,476,590 A | 10/1984 | Scales et al. |
| 4,552,751 A | 11/1985 | Inaba et al. |
| 5,387,419 A | 2/1995 | Levy et al. |

(Continued)

FOREIGN PATENT DOCUMENTS

| | | |
|---|---|---|
| CN | 101146486 A | 3/2008 |
| JP | 2004-537495 A | 12/2004 |

(Continued)

*Primary Examiner* — David W Bates
(74) *Attorney, Agent, or Firm* — Baker & Hostetler LLP (57) ABSTRACT

The present invention provides a drug eluting surgical screw and a method for manufacturing a drug eluting surgical screw. The drug eluting surgical screw may include a shaft having a threaded portion, a head having a drive recess disposed at a proximal end of the shaft, the drive recess having a reservoir region and a driver engagement region, and at least one or more drug eluting components disposed within the reservoir region of the drive recess in a manner that does not substantially impair a connection between a driver and the surgical screw when the driver is operably disposed within the driver engagement region, each of the at least one or more drug eluting components including a carrier matrix and a therapeutic agent, the therapeutic agent being at least 20 wt % of the drug eluting component prior to any implantation of the drug eluting surgical screw.

20 Claims, 5 Drawing Sheets

(56) References Cited

U.S. PATENT DOCUMENTS

| | | | |
|---|---|---|---|
| 5,985,317 A | 11/1999 | Venkateshwaran et al. | |
| 7,976,858 B2 | 7/2011 | Hotchkiss et al. | |
| 8,535,357 B2 | 9/2013 | Stone et al. | |
| 9,364,273 B2 | 6/2016 | Armbruster et al. | |
| 2002/0169162 A1* | 11/2002 | Smith | A61B 17/1615 514/248 |
| 2003/0139811 A1 | 7/2003 | Watson et al. | |
| 2005/0031665 A1 | 2/2005 | Watson et al. | |
| 2005/0101624 A1 | 5/2005 | Betts et al. | |
| 2005/0203612 A1 | 9/2005 | Bhat et al. | |
| 2005/0209244 A1 | 9/2005 | Prescott et al. | |
| 2005/0250838 A1* | 11/2005 | Challapalli | A61K 9/2031 514/419 |
| 2006/0106390 A1 | 5/2006 | Jensen et al. | |
| 2009/0088809 A1 | 4/2009 | Fisher et al. | |
| 2009/0163919 A1 | 6/2009 | Tarcha et al. | |
| 2010/0042167 A1 | 2/2010 | Nebosky et al. | |
| 2010/0249783 A1 | 9/2010 | Trieu | |
| 2012/0109111 A1 | 5/2012 | Li | |

FOREIGN PATENT DOCUMENTS

| | | |
|---|---|---|
| JP | 2012-016593 A | 1/2012 |
| TW | 402930 U | 8/2000 |

\* cited by examiner

DRUG ELUTING SURGICAL SCREW

CROSS REFERENCE TO RELATED APPLICATIONS

This application is a continuation of U.S. application Ser. No. 15/174,054, filed on Jun. 6, 2016, which is a continuation of U.S. application Ser. No. 13/800,342, filed Mar. 13, 2013, now U.S. Pat. No. 9,364,273, which claims the benefit of U.S. Provisional Patent Application No. 61/683,262, filed Aug. 15, 2012, the contents of each of which are incorporated by reference herein in their entireties.

BACKGROUND

The risks of infection following surgery are well documented. The presence of a foreign object such as a fracture fixation plate (e.g., an orthopedic fracture fixation plate) in the wound site may increase the risk of infection following surgery by providing a substrate for bacteria to adhere and proliferate, form a biofilm, and evade the host immune system. The risk of infection may increase in the case of open fractures where bacterial contamination of the wound prior to surgery is common. The consequences of implant related infection can be significant, with recurring infection leading to chronic osteomyelitis, impaired healing, and potentially limb amputation. Antibiotic eluting implants have been developed to address this concern.

SUMMARY

One embodiment of the present invention is a drug eluting surgical screw including a shaft having a threaded portion; a head having a drive recess disposed at a proximal end of the shaft, the drive recess having a reservoir region and a driver engagement region; and at least one or more drug eluting components disposed within the reservoir region of the drive recess in a manner that does not substantially impair a connection between a driver and the surgical screw when the driver is operably disposed within the driver engagement region, each of the at least one or more drug eluting components including a carrier matrix and a therapeutic agent, the therapeutic agent being at least about 20 wt % of the drug eluting component prior to any implantation of the drug eluting surgical screw.

In one embodiment, at least one of the at least one or more drug eluting components is configured to elute at least about 80% of its therapeutic agent over a three day period starting from when the drug eluting surgical screw is implanted into an animal.

In one embodiment, the concentration of the therapeutic agent of at least one of the at least one or more drug eluting components is between about 20 wt % and about 60 wt % of the at least one of the at least one or more drug eluting components prior to any implantation of the drug eluting surgical screw.

In one embodiment, the concentration of the therapeutic agent of at least one of the at least one or more drug eluting components is between about 20 wt % and about 40 wt % of the at least one of the at least one or more drug eluting components prior to any implantation of the drug eluting surgical screw.

In one embodiment, the reservoir region defines a reservoir volume, the drive recess defines a drive recess volume and the reservoir volume is from about 10% to about 12% of the drive recess volume. In one embodiment, the reservoir region of the drive recess is adjacent to the driver engagement region and the at least one or more drug eluting components do not extend into the driver engagement region. In one embodiment, the carrier matrix of at least one of the at least one or more drug eluting components includes a bioabsorbable polymer. In one embodiment, the bioabsorbable polymer includes polycaprolactone, polylactic acid, polyglycolic acid, polyethylene glycol, or a combination thereof. In another embodiment, the carrier matrix of at least one of the at least one or more drug eluting components includes polyethylene glycol, polyvinyl alcohol, glycerine, salts or a water soluble crystalline solid. In another embodiment, the carrier matrix of at least one of the at least one or more drug eluting components includes silica, hydroxyapatite, calcium phosphate, bioglass or a combination thereof. In another embodiment, the carrier matrix of at least one of the at least one or more drug eluting components includes a hydrophobic bioabsorbable polymer. In one embodiment, the hydrophobic bioabsorbable polymer includes a water swellable additive which swells with water after implantation into the body. In one embodiment, the carrier matrix of at least one of the at least one or more drug eluting components includes a nonabsorbable polymer. In one embodiment, the nonabsorbable polymer includes poly(methyl methacrylate). In one embodiment, the carrier matrix of at least one of the at least one or more drug eluting components includes a nonabsorbable polymer and a bioabsorbable polymer. In one embodiment, the bioabsorbable polymer includes polycaprolactone, polylactic acid, polyglycolic acid, polyethylene glycol, or a combination thereof. In one embodiment, the bioabsorbable polymer of at least one of the at least one or more drug eluting components includes an erodible ceramic. In one embodiment, the bioabsorbable polymer of at least one of the at least one or more drug eluting components includes a biostable ceramic. In one embodiment, the bioabsorbable polymer of at least one of the at least one or more drug eluting components includes a natural biopolymer. In one embodiment, the natural biopolymer includes gelatin, alginates, chitosan, collagen or hyaluronate.

In one embodiment, at least one of the one or more drug eluting components includes a nonabsorbable polymer and a soluble additive. In another embodiment, the nonabsorbable polymer includes poly(methyl methacrylate). In another embodiment, the soluble additive includes polyethylene glycol, polyvinyl alcohol, glycerine, salts or a water soluble crystalline solid.

In one embodiment, the therapeutic agent of at least one of the at least one or more drug eluting components includes a concentration gradient.

In one embodiment, the therapeutic agent of at least one of the at least one or more drug eluting components includes gentamicin. In another embodiment, the therapeutic agent of at least one of the at least one or more drug eluting components includes a steroid. In another embodiment, the steroid is an angiostatic steroid. In one embodiment, the therapeutic agent of at least one of the at least one or more drug eluting components includes an anti-inflammatory drug. In one embodiment, the therapeutic agent of at least one of the at least one or more drug eluting components includes an anti-proliferative compound. In one embodiment, the therapeutic agent of at least one of the at least one or more drug eluting components includes an antimycotic compound. In one embodiment, the therapeutic agent of at least one of the at least one or more drug eluting components includes an antimitotic compound. In one embodiment, the therapeutic agent of at least one of the at least one or more drug eluting components includes an antimetabolite compound. In one embodiment, the therapeutic agent of at least one of the at least one or more drug eluting components includes a pain-relieving drug. In one embodiment, the therapeutic agent of at least one of the at least one or more drug eluting components includes a corticosteroid. In one embodiment, the therapeutic agent of at least one of the at least one or more drug eluting components includes a non-steroidal anti-inflammatory agent. In one embodiment, the therapeutic agent of at least one of the at least one or more drug eluting components includes a co-drug. In one embodiment, the therapeutic agent of at least one of the at least one or more drug eluting components includes a growth factor. In one embodiment, the growth factor includes bone morphogenetic protein 2. In one embodiment, the therapeutic agent of at least one of the at least one or more drug eluting components includes a local anesthetic. In one embodiment, the local anesthetic includes lidocaine.

In one embodiment, the reservoir region is shaped and dimensioned to retain the at least one or more drug eluting components when the at least one or more drug eluting components are in a cured condition.

In one embodiment, the drug eluting surgical screw further includes a lip configured and dimensioned to retain the drug eluting component when the at least one or more drug eluting components are in a cured condition.

In one embodiment, the drug eluting surgical screw further includes at least two drug eluting components.

In one embodiment, the present invention is a method of manufacturing a drug eluting surgical screw, said method including mixing a drug eluting component with a solvent to form a solution, the drug eluting component including a carrier matrix and a therapeutic agent, the therapeutic agent being at least about 20 wt % of the drug eluting component prior to any implantation of the drug eluting surgical screw; heating the solution to evaporate the solvent and form a film; configuring at least a portion of the film to a size and shape that complements a drive recess of a surgical screw; placing the at least a portion of the film into the drive recess of the surgical screw; heating the at least a portion of the film to conform to the size and shape of a cross-section of the drive recess; and pressing the at least a portion of the heated film into the drive recess with a forming tool. A forming tool is preferably used to apply sufficient pressure to the heated film to create a bond between the film and the surgical screw.

In one embodiment, the present invention is a method of manufacturing a drug eluting surgical screw, said method including compounding a drug eluting component, the drug eluting component including a carrier matrix and a therapeutic agent, the therapeutic agent being at least about 20 wt % of the drug eluting component prior to any implantation of the drug eluting surgical screw; extruding the compounded drug eluting component to form a film; configuring at least a portion of the film to a size and shape that complements a drive recess of a surgical screw; placing the at least a portion of the film into the drive recess of the surgical screw; heating the at least a portion of the film to conform to the size and shape of a cross-section of the drive recess; and pressing the at least a portion of the heated film into the drive recess with a forming tool.

In one embodiment, the present invention is a method of manufacturing a drug eluting surgical screw, said method including compounding a drug eluting component, the drug eluting component including a carrier matrix and a therapeutic agent, the therapeutic agent being at least about 20 wt % of the drug eluting component prior to any implantation of the drug eluting surgical screw; compression molding the compounded drug eluting component to form a film; configuring at least a portion of the film to a size and shape that complements a drive recess of a surgical screw; placing the at least a portion of the film into the drive recess of the surgical screw; heating the at least a portion of the film to conform to the size and shape of a cross-section of the drive recess; and pressing the at least a portion of the heated film into the drive recess with a forming tool.

In one embodiment, each step is repeated sequentially to add an additional drug eluting component to the drive recess of the surgical screw.

In one embodiment, the drug eluting component is configured to elute at least about 80% of the therapeutic agent over a three day period starting from when the drug eluting surgical screw is implanted into an animal.

In one embodiment, the concentration of the therapeutic agent is between about 20 wt % and about 60 wt % of the drug eluting component prior to any implantation of the drug eluting surgical screw.

In one embodiment, the concentration of the therapeutic agent is between about 20 wt % and about 40 wt % of the drug eluting component prior to any implantation of the drug eluting surgical screw.

In one embodiment, the carrier matrix includes a bioabsorbable polymer. In one embodiment, the bioabsorbable polymer includes polycaprolactone, polylactic acid, polyglycolic acid, polyethylene glycol, or a combination thereof. In one embodiment, the carrier matrix includes polyethylene glycol, polyvinyl alcohol, glycerine, salts or a water soluble crystalline solid. In one embodiment, the carrier matrix includes silica, hydroxyapatite, calcium phosphate, bioglass or a combination thereof. In one embodiment, the carrier matrix includes a hydrophobic bioabsorbable polymer. In one embodiment, the hydrophobic bioabsorbable polymer includes a water swellable additive which swells with water after implantation into the body. In one embodiment, the carrier matrix includes a nonabsorbable polymer. In another embodiment, the nonabsorbable polymer includes poly(methyl methacrylate). In one embodiment, the carrier matrix includes a nonabsorbable polymer and a bioabsorbable polymer. In one embodiment, the bioabsorbable polymer includes polycaprolactone, polylactic acid, polyglycolic acid, polyethylene glycol, or a combination thereof. In one embodiment, the bioabsorbable polymer includes an erodible ceramic. In one embodiment, the bioabsorbable polymer includes a biostable ceramic. In one embodiment, the bioabsorbable polymer includes a natural biopolymer. In another embodiment, the natural biopolymer includes gelatin, alginates, chitosan, collagen or hyaluronate.

In one embodiment, the drug eluting component includes a nonabsorbable polymer and a soluble additive. In one embodiment, the nonabsorbable polymer includes poly(methyl methacrylate). In one embodiment, the soluble additive includes polyethylene glycol, polyvinyl alcohol, glycerine, salts or a water soluble crystalline solid.

In one embodiment, the drug eluting component includes a concentration gradient.

In one embodiment, the therapeutic agent includes gentamicin. In another embodiment, the therapeutic agent includes a steroid. In one embodiment, the steroid is an angiostatic steroid. In one embodiment, the therapeutic agent includes an anti-inflammatory drug. In one embodiment, the therapeutic agent includes an anti-proliferative compound. In one embodiment, the therapeutic agent includes an antimycotic compound. In one embodiment, the therapeutic agent includes an antimitotic compound. In one embodiment, the therapeutic agent includes an antimetabolite compound. In one embodiment, the therapeutic agent includes a pain-relieving drug. In one embodiment, the therapeutic agent includes a corticosteroid. In one embodiment, the therapeutic agent includes a non-steroidal anti-inflammatory agent. In one embodiment, the therapeutic agent includes a co-drug. In one embodiment, the therapeutic agent includes a growth factor. In one embodiment, the growth factor includes bone morphogenetic protein 2. In another embodiment, the therapeutic agent includes a local anesthetic. In one embodiment, the local anesthetic includes lidocaine.

One embodiment of the present invention is drug eluting surgical screw including a shaft having a threaded portion; a head having a drive recess disposed at a proximal end of the shaft, the drive recess having a reservoir region and a driver engagement region; and a drug eluting component disposed within the reservoir region of the drive recess in a manner that does not substantially impair a connection between a driver and the surgical screw when the driver is operably disposed within the driver engagement region, the drug eluting component including a carrier matrix and a therapeutic agent, the therapeutic agent being at least about 20 wt % of the drug eluting component prior to any implantation of the drug eluting surgical screw.

In one embodiment, the drug eluting component is configured to elute at least about 80% of the therapeutic agent over a three day period starting from when the drug eluting surgical screw is implanted into an animal. In another embodiment, the concentration of the therapeutic agent between about 20 wt % and about 60 wt % of the drug eluting component prior to any implantation of the drug eluting surgical screw. In another embodiment, the concentration of the therapeutic agent is between about 20 wt % and about 40 wt % of the drug eluting component prior to any implantation of the drug eluting surgical screw.

In one embodiment, the reservoir region defines a reservoir volume, the drive recess defines a drive recess volume and the reservoir volume is from about 10% to about 12% of the drive recess volume.

In another embodiment, the reservoir region of the drive recess is adjacent to the driver engagement region and the drug eluting component does not extend into the driver engagement region.

In certain embodiments, the carrier matrix includes polycaprolactone, polylactic acid, polyglycolic acid, polyethylene glycol, or a combination thereof.

In one embodiment, the therapeutic agent includes gentamicin.

In other embodiments, the reservoir region is shaped and dimensioned to retain the drug eluting component when the drug eluting component is in a cured condition.

In another embodiment, the drug eluting surgical screw further includes a lip configured and dimensioned to retain the drug eluting component when the drug eluting component is in a cured condition.

In one embodiment, the invention is directed to a method of manufacturing a drug eluting surgical screw, the method including mixing a drug eluting component with a solvent to form a solution, the drug eluting component including a carrier matrix and a therapeutic agent, the therapeutic agent being at least about 20 wt % of the drug eluting component prior to any implantation of the drug eluting surgical screw; heating the solution to evaporate the solvent and form a film; configuring at least a portion of the film to a size and shape that complements a drive recess of a surgical screw; placing the at least a portion of the film into the drive recess of the surgical screw; heating the at least a portion of the film to conform to the size and shape of a cross-section of the drive recess; and pressing the at least a portion of the heated film into the drive recess. A forming tool is preferably used to apply sufficient pressure to the heated film to create a bond between the film and the surgical screw.

In one embodiment, the drug eluting component is configured to elute at least about 80% of the therapeutic agent over a three day period starting from when the drug eluting surgical screw is implanted into an animal. In another embodiment, the therapeutic agent is from about 20 wt % to about 60 wt % of the drug eluting component prior to any implantation of the drug eluting surgical screw. In another embodiment, the concentration of the therapeutic agent is between about 20 wt % and about 40 wt % of the drug eluting component prior to any implantation of the drug eluting surgical screw.

In one embodiment, the carrier matrix includes polycaprolactone, polylactic acid, polyglycolic acid, polyethylene glycol, or a combination thereof.

In certain embodiments, the therapeutic agent includes gentamicin.

BRIEF DESCRIPTION OF THE DRAWINGS

The foregoing summary, as well as the following detailed description of embodiments of the present invention, will be better understood when read in conjunction with the appended drawings of exemplary embodiments. It should be understood, however, that the invention is not limited to the precise arrangements and instrumentalities shown.

In the drawings.

DETAILED DESCRIPTION OF ILLUSTRATIVE EMBODIMENTS

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

As shown generally in FIGS. 1A-7B, embodiments of the present invention are directed toward a surgical screw 100. In some embodiments, the surgical screw has a shaft 110. In one embodiment, the shaft 110 has a threaded portion 120. In certain embodiments, surgical screw 100 includes a head 140 disposed at a proximal end 130 of the shaft 110. In one embodiment, the head 140 has a drive recess 150. In one embodiment, the drive recess 150 is hexagonally shaped. Although illustrated as being hexagonally shaped, it is envisioned that the shape of the drive recess 150 may be configured in any manner suitable for distributing an insertion force throughout the screw, e.g., other polygonal or generally polygonal shapes, semi-circular, slotted, cross-recessed, torx star, or multiple round holes.

Figure 1A:
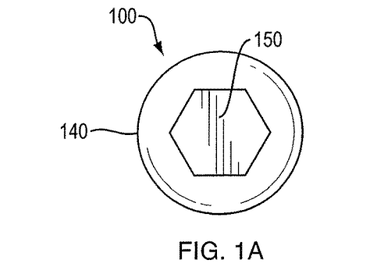
FIG. 1A is a top view and FIG. 1B is a side perspective partial cross-sectional view of a surgical screw according to one embodiment.
Figure 1B:
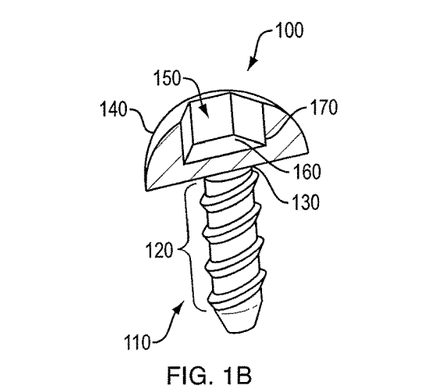
Figure 2A:
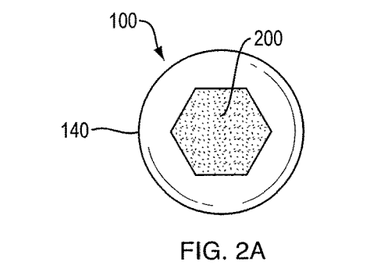
FIG. 2A is a top view and FIG. 2B is a side perspective partial cross-sectional view of an embodiment of a surgical screw having a drug eluting matrix in the drive recess.
Figure 2B:
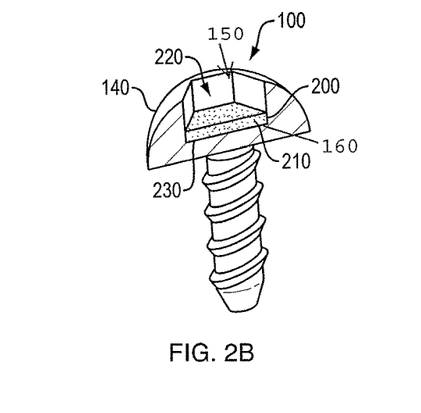

Referring to FIG. 2B, the drive recess 150, in certain embodiments, has a reservoir region 160 and a driver engagement region 170. As seen by comparing FIGS. 2B and 6B, in certain embodiments, the reservoir region 160 can be of varied shape and depth. The reservoir region 160 can be any region of the head 140 of the screw 100 that can be coated with a drug eluting component 200 in a manner that will not substantially impair a connection between a driver and the surgical screw 100 when the driver is operably disposed within the driver engagement region 170. The driver engagement region 170 can be any region of the head 140 of the screw 100, either coated or uncoated with the drug eluting component 200, that is engageable with a driver when the driver is operably disposed within the head 140. The reservoir region 160 and driver engagement region 170 need not be exclusive and may overlap.

In one embodiment, the reservoir region 160 defines a reservoir volume 210, the drive recess 150 defines a driver recess volume 220 and the reservoir volume 210 is from about 10% to about 12% of the driver recess volume. In other embodiments, the reservoir volume 210 is about 8%, about 8.5%, about 9%, about 9.5%, about 10%, about 10.5%, about 11%, about 11.5%, about 12%, about 12.5%, about 13%, about 13.5%, about 14% or any range determinable from the preceding percents (for example, about 8% to about 9.5% or about 8.5% to about 13%) of the driver recess volume 220.

In certain embodiments, multiple layers of drug eluting components can be layered into the reservoir region 160 of the drive recess 150 to allow for multiple therapeutic agents to be released at different rates, sequentially, or simultaneously in different concentrations. One of the layers may not contain a therapeutic agent, but serve as a barrier layer to inhibit diffusion of the drug. Exemplary materials which could act as a barrier layer include bioabsorbable polymers such as polycaprolactone or polyglycolide, natural fatty acids such as palmitic acid or stearic acid, and natural biopolymers such as collagen or alginate.

Figure 3A:
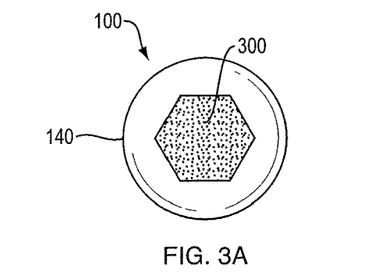
FIG. 3A is a top view and FIG. 3B is a side perspective partial cross-sectional view of an embodiment of a surgical screw having a drug eluting matrix in the drive recess with a diffusion barrier layer.
Figure 3B:
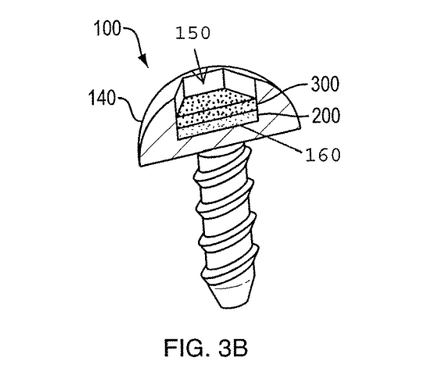

As shown in FIG. 3B, in one embodiment, both a diffusion barrier layer 300 and a drug eluting component 200 are disposed within the reservoir region 160 of the drive recess 150.

Figure 4A:
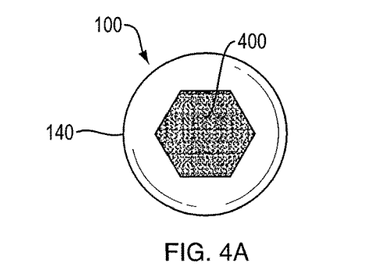
FIG. 4A is a top view and FIG. 4B is a side perspective partial cross-sectional view of an embodiment of a surgical screw having two layers of drug eluting matrix in the drive recess, containing two different drugs.
Figure 4B:
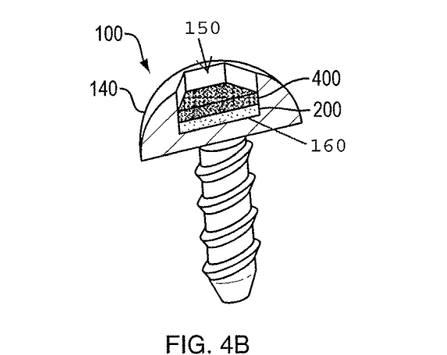

Further, FIG. 4B illustrates an exemplary view of the surgical screw where two drug eluting components, drug eluting component 200 and drug eluting component 400, are disposed within the reservoir region 160 of the drive recess 150. In some embodiments, drug eluting component 200 and drug eluting component 400 include different therapeutic agents. In other embodiments, the drug eluting component 200 and drug eluting component 400 are configured to elute a therapeutic agent at differing release rates.

Figure 5A:
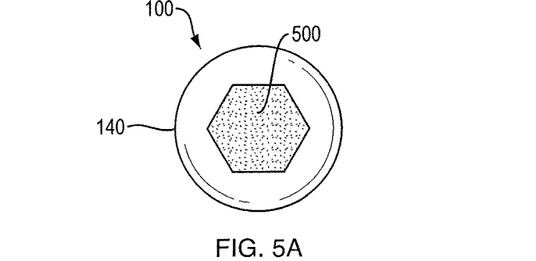
FIG. 5A is a top view and FIG. 5B is a side perspective partial cross-sectional view of an embodiment of a surgical screw having a drug eluting matrix in the drive recess with a graded drug concentration.
Figure 5B:
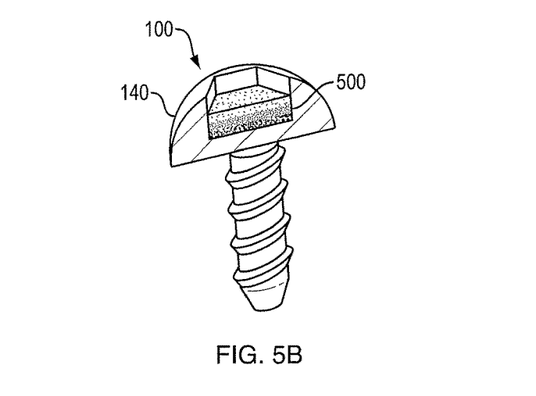
Figure 6A:
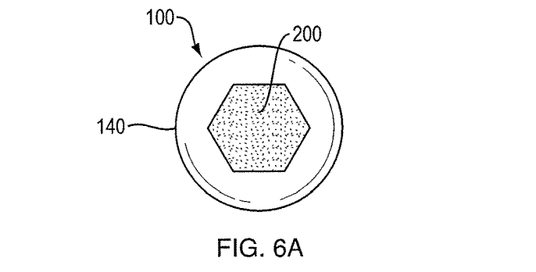
FIG. 6A is a top view and FIG. 6B is a side perspective partial cross-sectional view of an embodiment of a surgical screw having an additional reservoir added to the bottom of the drive recess and having a drug eluting matrix in the drive recess.
Figure 6B:
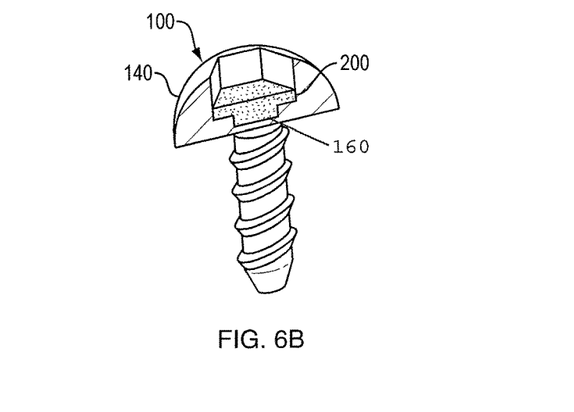

FIG. 5B shows an exemplary embodiment of the invention having a drug eluting component with a graded concentration 500, e.g., a therapeutic agent being less concentrated at the surface and gradually more concentrated at deeper depths or, alternatively, a therapeutic agent being more concentrated at the surface and gradually less concentrated at deeper depths.

As shown generally in FIG. 2B, one embodiment of the present invention includes a drug eluting component 200 disposed within the reservoir region 160 of the drive recess 150. In certain embodiments, the drug eluting component 200 is positioned in a manner so that it does not substantially impair a connection between a driver and the surgical screw 100 when the driver is operably disposed within the driver engagement region 170. For example, as shown in FIG. 2B, the drug eluting component 200 may be positioned at the base 230 of the head 140. In other embodiments, the reservoir region 160 of the drive recess 150 is adjacent to the driver engagement region 170 and the drug eluting component 200 does not extend into the driver engagement region 170.

Figure 7A:
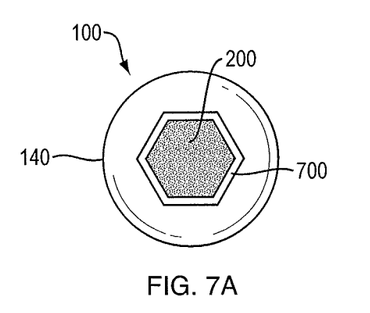
FIG. 7A is a top view and FIG. 7B is a side perspective partial cross-sectional view of an embodiment of a surgical screw having a lip configured and dimensioned to retain a drug eluting component when the drug eluting component is in a cured condition; and, FIG. 8 is a schematic side perspective cross-sectional view of a surgical screw securing a fracture fixation implant to bone according to an embodiment of the disclosure.
Figure 7B:
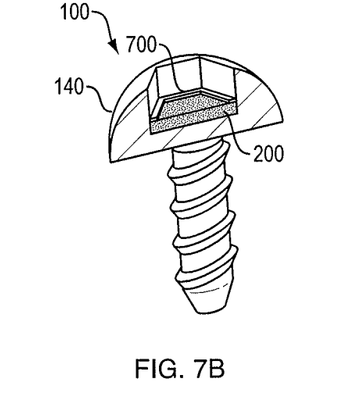

In one embodiment, the reservoir region 160 is shaped and dimensioned to retain the drug eluting component 200 when the drug eluting component 200 is in a cured condition. For example, as shown in FIGS. 7A and 7B, the surgical screw 100 includes a lip 700 configured and dimensioned to retain the drug eluting component 200 when the drug eluting component 200 is in a cured condition.

In one embodiment, the drug eluting component 200 includes a carrier matrix containing a therapeutic agent. In certain embodiments, the carrier matrix includes a material that facilitates the release rate of the therapeutic agent into the body, e.g., a polymer, ceramic, or hydrogel. In one embodiment, the carrier matrix includes a bioabsorbable polymer, e.g., polycaprolactone, polylactic acid, polyglycolic acid, polyethylene glycol, or a combination thereof.

In other embodiments, the carrier matrix includes a soluble additive which dissolves at a controlled rate, generating pores through which the therapeutic agent can elute. Examples of a soluble additive would include polyethylene glycol, polyvinyl alcohol, glycerine, salts or water soluble crystalline solids. By varying the amount of soluble additive, the elution rate of the therapeutic agent may be modified. Certain embodiments having differing release rates, can be achieved by having multiple drug eluting components, each having differing bioabsorbable matrices having differing soluble additives.

In another embodiment, the carrier matrix includes a hydrophobic bioabsorbable polymer that contains a water swellable additive that swells with water after implantation into the body, allowing the therapeutic agent to be released at an increased rate. By varying the amount of water swellable additive, the elution rate of the therapeutic agent may be modified.

In one embodiment, the carrier matrix includes a nonabsorbable polymer, e.g., poly(methyl methacrylate).

In another embodiment, the carrier matrix includes a nonabsorbable polymer and a soluble additive, e.g., polyethylene glycol, polyvinyl alcohol, glycerine, salts or water soluble crystalline solids. The soluble additive dissolves at a controlled rate, generating pores in the nonabsorbable matrix through which a therapeutic agent can elute.

In certain embodiments, the carrier matrix includes a blend of bioabsorbable polymer and nonabsorbable polymer.

In other embodiments, the carrier matrix includes an erodible or biostable ceramic, e.g., silica, hydroxyapatite, calcium phosphate, bioglass, or a combination thereof.

In one embodiment, the carrier matrix includes a natural biopolymer, e.g., gelatin, alginates, chitosan, collagen or hyaluronate.

In one embodiment, the therapeutic agent includes an antibiotic or a combination of multiple antibiotics. In one embodiment, the therapeutic agent includes gentamicin.

In other embodiments, the therapeutic agent includes steroids, anti-inflammatory drugs, anti-proliferative compounds, antimycotic compounds, an antimitotic compounds, antimetabolite compounds, pain-relieving drugs, corticosteroids, angiostatic steroids, non-steroidal anti-inflammatory agents, and/or co-drugs.

In certain embodiments, the therapeutic agent includes a growth factor, e.g., bone morphogenetic protein 2 (BMP-2). In other embodiments, the therapeutic agent includes a local anesthetic, e.g., lidocaine.

The therapeutic agent, in certain embodiments, can either be dissolved completely into the material that facilitates its release into the body or remain as discrete particles within that material.

In one embodiment, the therapeutic agent constitutes at least about 20 wt % of the drug eluting component prior to any implantation of the drug eluting surgical screw 100. In one embodiment, the therapeutic agent constitutes between about 20 wt % and about 60 wt % of the drug eluting component prior to any implantation of the drug eluting surgical screw 100. In one embodiment, the therapeutic agent constitutes between about 20 wt % and about 40 wt % of the drug eluting component prior to any implantation of the drug eluting surgical screw 100. In other embodiments, the therapeutic agent constitutes about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, about 60 wt % or any range determinable from the preceding weight percents (for example, about 51 wt % to about 55 wt % or about 30 wt % to about 52 wt %) of the drug eluting component prior to any implantation of the drug eluting surgical screw 100.

In one embodiment, the drug eluting component 200 is configured to elute at least about 80% of the therapeutic agent over a three day period starting from when the drug eluting surgical screw 100 is implanted into the animal. In other embodiments, the drug eluting component 200 is configured to elute about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100% or any range determinable from the preceding percents (for example, about 50% to about 77% or about 85% to about 94%) of the therapeutic agent over a one day, two day, three day, four day, five day, six day, seven day or any range determinable from the preceding days (for example, 1-3 days or 3-4 days) period starting from when the drug eluting surgical screw 100 is implanted into the animal.

In one embodiment, the present invention includes a method of manufacturing a drug eluting surgical screw 100. In one embodiment, the method includes forming a film derived from a drug eluting component. In one embodiment, a film is formed by mixing a drug eluting component with a solvent to form a solution and heating the solution to evaporate the solvent and form a film. In another embodiment, a film is formed by subjecting a drug eluting component to a melting process, e.g., by a process including compounding, and then subjecting the melted drug eluting component to extrusion or compression molding. In one embodiment, after the film has been formed, the method includes, configuring at least a portion of the film to a size and shape that complements a drive recess of a surgical screw. In one embodiment, the method further includes placing the at least a portion of the film into the drive recess 150 of the surgical screw 100. In one embodiment, after placing the at least a portion of the film into the drive recess 150, heating the at least a portion of the film to conform to the size and shape of a cross-section of the drive recess. In one embodiment, after heating the at least a portion of the film, the method includes, pressing the at least a portion of the heated film into the drive recess 150. In one embodiment, a forming tool, e.g., a screwdriver with an end shaped to fit within the drive recess, is used, e.g., used by pressing the heated film into the drive recess 150, to form a sufficient bond between the at least a portion of the heated film and the drive recess side walls.

In one embodiment, the method of manufacturing a drug eluting surgical screw 100 described above is repeated to create a drug eluting surgical screw 100 having multiple layers of drug eluting components, e.g., as shown in FIGS. 4A and 4B.

Figure 8:
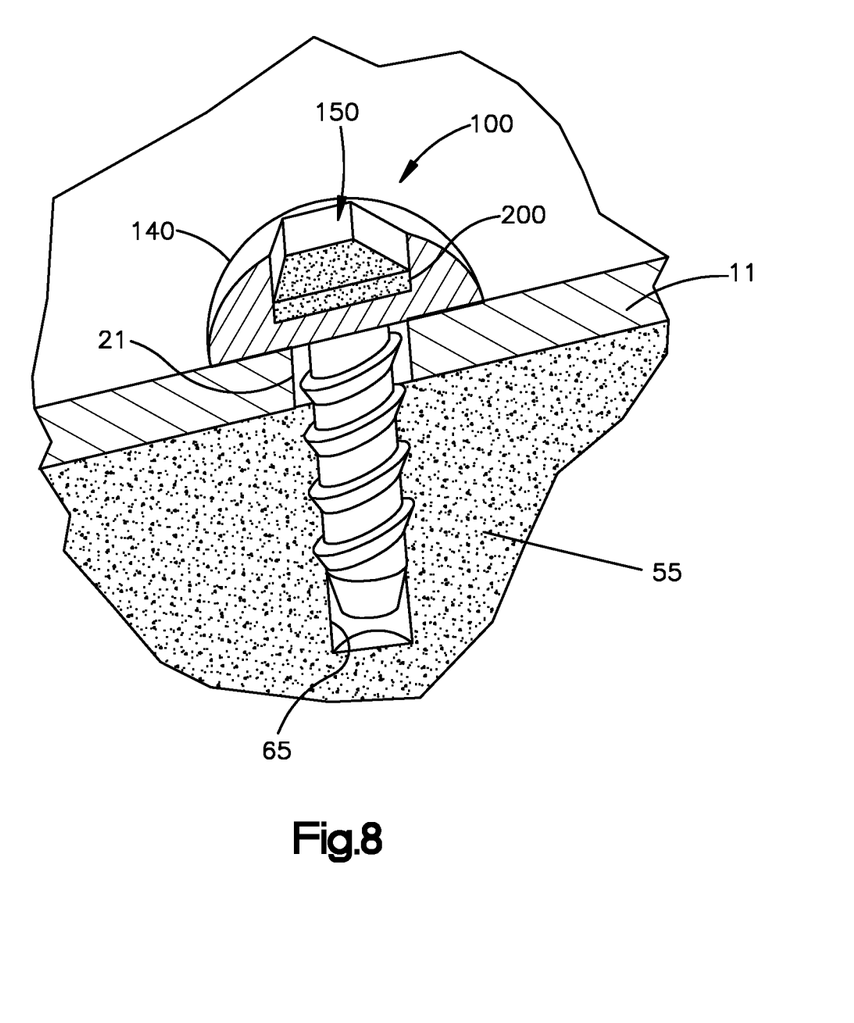

Referring to FIG. 8, in one embodiment (shown schematically), the present invention includes a method of using the drug eluting surgical screw 100 to secure an implant 11, e.g., a fixation plate. In one embodiment, the method includes forming a cavity 65 in a bone 55 for receiving the drug eluting screw 100, e.g., via drilling. The method further may include placing an implant 11 having an aperture 21 against the bone 55, the aperture 21 being aligned with the cavity 65. The method further may include using a driver to fix the drug eluting screw 100 to the bone 55, whereby the implant 11 is held between the bone 55 and the head 140 of the screw.

Still referring to FIG. 8, in one embodiment the present invention includes a method of reducing the risk of infection following surgery. In one embodiment, the method includes using the drug eluting surgical screw 100 to secure an implant 11 in an animal following surgery. In certain embodiments, the drug eluting component 200 will elute an antibiotic, e.g., gentamicin, locally at the surface of the implant 11 thereby reducing the risk of infection.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed:

1. An antibiotic eluting system comprising:
   a drug eluting component comprising a carrier matrix and a therapeutic agent, the therapeutic agent compounded within the carrier matrix, and wherein the therapeutic agent includes at least one antibiotic, and,
   an implant having a head disposed at a proximal end, the head defining a recess and the recess including a reservoir region;
   wherein the drug eluting component is disposed within the reservoir region, and,
   wherein the drug eluting component has an elution release rate configured to elute the at least one antibiotic locally along a surface of the implant at a rate of at least about 50% by weight of the at least one antibiotic within 7 days after implantation so as to reduce the risk of infection.

2. The antibiotic eluting system of claim 1, wherein the carrier matrix includes silica, hydroxyapatite, calcium phosphate, bioglass, or a combination thereof.

3. The antibiotic eluting system of claim 1, wherein the carrier matrix includes a nonabsorbable polymer.

4. The antibiotic eluting system of claim 1, wherein the carrier matrix includes a bioabsorbable polymer.

5. The antibiotic eluting system of claim 4, wherein the bioabsorbable polymer is a hydrophobic bioabsorbable polymer and includes a water swellable additive.

6. The antibiotic eluting system of claim 4, wherein the carrier matrix further includes a nonabsorbable polymer.

7. The antibiotic eluting system of claim 4, wherein the carrier matrix further includes an erodible ceramic.

8. The antibiotic eluting system of claim 3, wherein the carrier matrix further includes a soluble additive.

9. The antibiotic eluting system of claim 1, wherein the drug eluting component is disposed as a layer within the reservoir region.

10. The antibiotic eluting system of claim 9, further comprising one or more additional drug eluting components disposed as a layer in the reservoir region.

11. The antibiotic eluting system of claim 1, further comprising a barrier layer disposed in the recess, the barrier layer configured to inhibit diffusion of the therapeutic agent from the drug eluting component.

12. The antibiotic eluting system of claim 1, wherein the therapeutic agent is disposed in the drug eluting component in a concentration gradient extending from a surface of the drug eluting component through the depth of the drug eluting component.

13. The antibiotic eluting system of claim 1, wherein the drug eluting component is a film.

14. The antibiotic eluting system of claim 1, wherein the therapeutic agent includes multiple antibiotics, such that the at least one antibiotic is a first antibiotic and an additional antibiotic of the multiple antibiotics is a second antibiotic.

15. The antibiotic eluting system of claim 1, wherein the therapeutic agent is dissolved within the carrier matrix.

16. The antibiotic eluting system of claim 1, wherein the therapeutic agent is disposed as discrete particles within the carrier matrix.

17. The antibiotic eluting system of claim 14, wherein the first antibiotic is dissolved within the carrier matrix, and the second antibiotic is disposed as discrete particles within the carrier matrix.

18. The antibiotic eluting system of claim 14, wherein the second antibiotic is dissolved within the carrier matrix, and the first antibiotic is disposed as discrete particles within the carrier matrix.

19. The antibiotic eluting system of claim 14, wherein the first antibiotic has a first concentration in the drug eluting component and the second antibiotic has a second concentration in the drug eluting component that is different from the first concentration.

20. The antibiotic eluting system of claim 14, wherein the first antibiotic has a first elution release rate from the drug eluting component and the second antibiotic has a second elution release rate from the drug eluting component that is different from the first elution release rate.

* * * * *